United States Patent [19]

Willard, Sr.

[11] 4,067,715
[45] * Jan. 10, 1978

[54] METHOD OF TRANSPLANTING PLANTS

[75] Inventor: John Wesley Willard, Sr., Rapid City, S. Dak.

[73] Assignee: CAW Industries, Inc., Rapid City, S. Dak.

[ * ] Notice: The portion of the term of this patent subsequent to July 8, 1992, has been disclaimed.

[21] Appl. No.: 750,394

[22] Filed: Dec. 14, 1976

Related U.S. Application Data

[63] Continuation-in-part of Ser. No. 593,712, July 7, 1975, which is a continuation-in-part of Ser. No. 317,097, Dec. 20, 1972, Pat. No. 3,893,943, which is a continuation of Ser. No. 108,198, Jan. 20, 1971, abandoned.

[51] Int. Cl.$^2$ ............................................. C05F 11/02
[52] U.S. Cl. ............................................. 71/24; 71/63; 71/64 C; 71/64 SC; 47/DIG. 11
[58] Field of Search ....................... 44/1 R, 1 B, 6, 27; 252/446; 71/1, 24, 27, 63, 64 C, 64 SC; 47/1 R, 48.5, 58, DIG. 10, DIG. 11

[56] References Cited

U.S. PATENT DOCUMENTS

| | | | |
|---|---|---|---|
| 3,272,753 | 9/1966 | Wixon | 252/532 X |
| 3,350,319 | 10/1967 | Schonfeldt | 252/532 X |
| 3,351,558 | 11/1967 | Zimmerer | 252/532 X |
| 3,377,293 | 4/1968 | Shephard | 252/313 S |
| 3,453,144 | 7/1969 | Morgan et al. | 252/532 X |
| 3,657,151 | 4/1972 | Noble | 252/453 X |
| 3,893,943 | 7/1975 | Willard, Sr. | 252/451 X |

*Primary Examiner*—Charles N. Hart
*Assistant Examiner*—Ferris H. Lander
*Attorney, Agent, or Firm*—L. S. Van Landingham, Jr.

[57] ABSTRACT

The roots of plants being transplanted are intimately contacted with water containing a catalytically effective amount of a novel catalyst. In a preferred variant, the water may also contain water soluble catalyst treated lignite. The catalyst is prepared by a process including the steps of admixing a water soluble alkali metal silicate with an aqueous medium containing carefully controlled amounts of water soluble substances which are sources of calcium ion and magnesium ion, reacting the same to produce an aqueous colloidal suspension of the reaction product, admixing a micelle forming surfactant with the aqueous medium, and agitating the aqueous medium containing the colloidal particles and surfactant to form catalyst-containing micelles. The preparation of the novel catalyst and the water soluble catalyst treated lignite is described in detail hereinafter. The transplanted plants grow more vigorously and are more resistant to disease and/or adverse environmental conditions.

22 Claims, No Drawings

METHOD OF TRANSPLANTING PLANTS

RELATED APPLICATIONS

This application is a continuation-in-part of copending application Ser. No. 593,712, filed July 7, 1975 on behalf of John W. Willard, Sr. for A PROCESS FOR TREATING SOLID CARBONACEOUS FOSSIL FUELS AND THE PRODUCTS THUS PREPARED. Application Ser. No. 593,712 was a continuation-in-part of application Ser. No. 317,097, now U.S. Pat. No. 3,893,943, filed Dec. 20, 1972, for NOVEL CATALYST AND PROCESS FOR PREPARING THE SAME. Application Ser. No. 317,097, was a continuation of application Ser. No. 108,198, now abandoned, filed Jan. 20, 1971, for NOVEL CATALYST AND PROCESS FOR PREPARING THE SAME.

THE BACKGROUND OF THE INVENTION

1. The Field of the Invention

This invention broadly relates to a method of transplanting plants. In some of its more specific aspects, the invention is concerned with a method whereby plants may be transplanted to assure a higher survival rate initially, and to thereafter achieve more vigorous growth and increased resistance to disease and/or adverse environmental conditions.

2. The Prior Art

Transplanting is an important method of propagating many species of plants. Examples of plants which may be propagated by transplanting include garden plants such as tomatoes, peppers, cabbage, broccoli and egg plant, vines such as ivy, honeysuckle and periwinkle, flowers such as marigolds, zinnias and pansies, and shrubbery and trees such as juniper, cedar, holly, pine, poplar and maple.

In practicing the basic prior art method, usually seedlings or young plants are planted in soil at the proper depth and spacing for the species being transplanted. The plants are often watered with plain water at the time of transplanting, but natural rain fall may be relied upon to provide sufficient moisture in some instances and especially when the soil is wet at the time of transplanting. Even under optimum conditions, the plants are subjected to marked stress and/or shock over the period immediately following transplanting and until sufficient new feeder roots form to support life. The survival rate is often low and especially when there is insufficient moisture such as during a drought. The surviving plants also tend to grow slowly, if at all, during the period immediately following transplanting.

A number of attempts have been made heretofore to overcome the above mentioned limitations and disadvantages of propagating plants by transplanting. One prior art proposal involves frequent watering with plain water over the critical period following transplanting and until the plants are well established. This method is expensive and time consuming, and it requires a large volume of water which is not always available during dry weather or in arid areas. Still another proposal involves the use of rooting hormones which tend to promote the growth of feeder roots following transplanting. Rooting hormones aid in establishing the plants in a shorter period of time, but it is still advisable to water the transplanted plants frequently. While these and other prior art proposals are useful in transplanting a number of plant species, they are not entirely satisfactory in all instances and especially when the plants are normally hard to transplant and establish even under optimum conditions. The prior art proposals also do not have a beneficial effect on the transplanted plants throughout their lifespan. Thus, established plants transplanted by the prior art methods do not grow more vigorously or yield more, nor do they have more resistance to disease or adverse environmental conditions. Any beneficial effect gained by transplanting plants by the improved prior art methods are limited, as a general rule, to the period shortly following transplanting as distinguished from long term benefits.

It will be apparent from the foregoing that the art has long sought an entirely satisfactory method of propagating plants by transplanting which not only assures faster recovery from the stress and/or shock of transplanting, earlier establishment and a higher survival rate, but which also simultaneously provides plants characterized by increased vigor and resistance to disease and adverse environmental conditions over their lifespan. However, such a method was not available prior to the present invention.

THE SUMMARY OF THE INVENTION

The present invention provides a novel method of propagating plants by transplanting which results in a combination of unusual and unexpected benefits over the critical period immediately following transplanting, and thereafter over the lifespan of the plants. This is accomplished both inexpensively and conveniently by intimately contacting the roots of plants being transplanted with water containing a catalytically effective amount of a novel catalyst. The transplanted plants overcame the stress and shock of transplanting faster, and they are established quicker, have a higher survival rate and commence to grow earlier and more vigorously. The established transplanted plants also continue to grow more vigorously and are more resistant to disease or adverse environmental conditions over their lifespan. Yields are higher in instances where the plants are grown commercially for food or fiber, and the plants have a more pleasing appearance in instances where they are grown for decorative purposes. In a preferred variant, the water intimately contacted with the roots of the plants being transplanted also contains water soluble catalyst treated lignite. Reference may be had to the following detailed description and the specific examples for preferred variants and embodiments of the invention, and for presently preferred processes for preparing the aforementioned novel catalyst and catalyst treated lignite.

The Detailed Description of the Invention Including Certain Presently Preferred Variants and Embodiments Thereof In practicing the present invention, the roots of plants being transplanted are intimately contacted with water containing a catalytically effective amount of the novel catalyst described hereinafter. The water also may contain lignite which has been pretreated with the catalyst until it is soluble to thereby further improve the results. It will be appreciated that there are certain presently known preferred variants and embodiments of the invention which produce exceptionally good results, and that such preferred variants and embodiments will be discussed in greater detail hereinafter and/or illustrated in the examples.

The water that is intimately contacted with the roots of plants being transplanted need contain only a catalytically effective amount of the catalyst, but much larger amounts may be present as the catalyst appears to be harmless when present in reasonable amounts. For example, the water usually contains about 0.000001–1000 parts per million (ppm) of the catalyst, and about 0.00001–200 ppm often produces very good results. In some instances, the water contains about 0.00005–100 ppm of the catalyst, and in other instances, about 0.005–50 ppm of the catalyst. Very small amounts of the catalyst may be present in the water in still other instances, such as about 0.00001–5 ppm or about 0.01–1 ppm. For even better results, the water also contains water soluble catalyst treated lignite in an amount of, for example, about 0.000001–1000 ppm, or about 0.00001–200 ppm. In other instances, the water may contain about 0.00005–100 ppm, or about 0.005–50 ppm, of the catalyst treated lignite. In still other instances, the water need contain only about 0.00001–5 ppm, and often only about 0.01–1 ppm of the catalyst treated lignite. As is apparent from the above, the catalyst treated lignite also need be present in only substantially catalytic amounts, but much larger amounts may be present as it likewise appears to be harmless in reasonable amounts.

The catalyst and catalyst treated lignite are prepared as described hereinafter, and the quantities of the catalyst and the catalyst treated lignite are calculated by weight and on a dry solids basis. The catalyst treated lignite often contains the catalyst which was used in its preparation and, in such instances, the weight of catalyst solids initially present is included in the calculations to determine the total amount of catalyst solids. When the catalyst treated lignite is present, the weight ratio of catalyst solids to catalyst treated lignite solids may vary over wide ranges such as, for example, from about 1:200 to 200:1 in most instances, and from about 1:50 to 50:1 in some instances. Usually, the weight ratio of catalyst solids to catalyst treated lignite solids is about 1:10 to 1:30, and often is about 1:20.

The water containing the catalyst and/or catalyst treated lignite may be intimately contacted with the roots of plants being transplanted in any convenient manner. For example, the roots may be merely sprayed or dipped in water containing the catalyst and/or catalyst treated lignite, or the roots may be allowed to remain therein for a substantial period of time such as from 5 minutes to one hour, and then the plant is transplanted in the normal manner. In another variant, the roots are placed in prepared openings in the soil, then sprayed or wetted with water containing the catalyst and/or catalyst treated lignite in place, and then the treated roots are covered with soil to the proper depth. It is also possible to place the roots at the proper depth in soil, sand, vermiculite, or other absorbent particulate material which is known to be suitable for transplanting, and then maintain the same moist by watering exclusively or periodically with water containing the catalyst and/or catalyst treated lignite. In practicing this latter variant, it is possible to use, for example, 50–99% of plain water for maintaining the desired moisture level, and then use, for example, 50–1% of water containing the catalyst and/or catalyst treated lignite on a periodic basis.

Regardless of the specific technique that is used, it is only necessary to intimately contact the roots of plants to be transplanted with water containing the catalyst and/or catalyst treated lignite. The prior art practices followed when transplanting seedlings or young plants of a specific plant species may be followed in practicing the present invention with the exception of intimately contacting the roots of the plants with water containing the catalyst and/or catalyst treated lignite. Such prior art practices are well known, and there are numerous publications in this field. For example, the United States Department of Agriculture publishes and distributes to the public a number of publications concerned with the propagation of plants by transplanting, the disclosures of which are incorporated herein by reference. The procedures recommended therein also may be followed in practicing the present invention with the exception of intimately contacting the roots of the plants with water containing the catalyst and/or catalyst treated lignite immediately before, during or after transplanting.

As a general rule, the roots of plants of species known to be difficult to transplant should be intimately contacted with water containing, within the aforementioned ranges, higher concentrations of the catalyst and/or catalyst treated lignite and/or over longer periods of time or at more frequent intervals. Sufficient moisture is maintained in the transplanting medium to assure that the plant does not dehydrate until it is established. Surprisingly, less moisture is required for transplanting when practicing the present invention than when practicing the prior art methods as the transplanted plants appear to be more resistant to drought, and/or the transplanting medium tends to hold moisture better due to the presence of the catalyst and/or catalyst treated lignite.

When practicing the present invention, new feeder roots appear earlier following transplanting. The roots are longer, stronger and appear in larger numbers, and are more capable of supplying the plant with water and nutrients. The transplanted plants have a higher survival rate, overcome stress and shock due to transplanting quicker, and commence to grow earlier and more vigorously. The presence of the catalyst and/or catalyst treated lignite also has a beneficial effect on the transplanted plants throughout their lifespan. The established transplanted plants continue to grow more vigorously, and are more resistant to disease or adverse environmental conditions such as insufficient moisture, excessive moisture, insufficient sun, too much sun, and insufficient plant nutrients. Yields are higher with respect to plants producing a commercially valuable commodity such as food or fiber, and plants grown for decorative purposes such as shrubbery and flowers are more beautiful. Thus, the present invention provides initial benefits in that the survival rate is higher and the plants overcome the adverse effects of transplanting faster, and long term benefits in that the life processes of the established transplanted plants are favorably influenced or promoted throughout their lifespan. This unusual and unexpected combination of beneficial results has not been achieved heretofore by the prior art methods of transplanting.

The preparation of the novel catalyst or synergist of the invention is described immediately hereinafter, and the preparation of the cataylst treated lignite is described thereafter. In instances where an aqueous suspension or solution of the catalyst and/or the catalyst treated lignite is used in practicing the method of the invention, then the concentration of the catalyst and/or the catalyst treated lignite often may be as set out hereinafter

PREPARATION OF THE CATALYST

The catalyst used in practicing the present invention may be prepared as described below. In the presently preferred process for preparing an aqueous suspension of the catalyst, a water soluble alkali metal silicate is admixed and reacted with an aqueous solution of a water soluble dissolved substance which is a source of calcium ion and a water soluble dissolved substance which is a source of magnesium ion to produce a finely divided or colloidal suspension of the reaction product. The aqueous solution contains the dissolved substances initially in amounts to provide between about $1 \times 10^{-4}$ and $1 \times 10^{-1}$ mole per liter each of calcium ion and magnesium ion, preferably between about $1 \times 10^{-3}$ and $1 \times 10^{-2}$ mole per liter, and for still better results between $1 \times 10^{-3}$ and $6 \times 10^{-}$ mole per liter. The dissolved substances should also be present in amounts to provide a molar ratio of calcium ion to magnesium ion between about 2.0:1.0 and 1.0:2.0, and preferably about 1.5:1.0 and 1.0:1.5. For best results, the aqueous medium should contain the dissolved substances in amounts to provide between about $2.5 \times 10^{-3}$ and $3.0 \times 10^{-3}$ mole per liter each of calcium ion and magnesium ion, and the molar ratio of calcium ion to magnesium ion should be about 1.0:1.0, e.g., $2.9 \times 10^{-3}$ mole per liter of calcium ion and $2.7 \times 10^{-3}$ mole per liter of magnesium ion. The alkali metal silicate should have an alkali metal oxide to silicon dioxide ratio between about 0.9:1.0 and less than 2.0:1.0, and preferably between about 0.9:1.0 and 1.2:1.0. The alkali metal silicate should be admixed with the aqueous medium in an amount of about 0.05-2 moles per liter, preferably about 0.1-1 mole per liter, and for still better results about 0.2-0.5 mole per liter. For best results, the alkali metal silicate should be an alkali metasilicate having an alkali metal oxide to silicon dioxide ratio of about 1:1, and it should be admixed with the aqueous medium in an amount to provide about 0.2-0.3 mole per liter, e.g., about 0.25 mole per liter.

Examples of sources of calcium ion and magnesium ion for use in preparing the aqueous solution include mineral acid salts such as the halides, sulfates, bisulfates, nitrates, and nitrates of calcium and magnesium. The chlorides are usually the preferred halides, and both calcium and magnesium chloride are soluble and may be used. Magnesium sulfate and bisulfate are soluble and often are the preferred sources of magnesium ion. Calcium sulfate is only slightly soluble in water and usually is not a preferred source of calcium ion, but calcium bisulfate is somewhat more soluble. While calcium and magnesium nitrite or nitrate are soluble in water and may be used, these substances are not preferred in most instances. The sources of calcium ion and magnesium ion are dissolved in the aqueous medium in amounts to provide calcium ion and magnesium ion within the above ranges. Complete ionization is assumed when calculating the quantities to be dissolved and any desired order of addition is satisfactory. For example, the source of calcium ion may be added to the aqueous medium before, during or after the source of magnesium ion.

The alkali metal silicate to be admixed with the aqueous medium is preferably a water soluble sodium or potassium silicate having an alkali metal oxide ($M_2O$) to silicon dioxide ($SiO_2$) mole ratio between about 0.9:1.0 and less than 2.0:1.0, and preferably between about 0.9:1.0 and 1.2:1.0. The best results are usually obtained with an alkali metal metasilicate having an alkali metal oxide to silicon dioxide ratio of about 1:1. Hydrated alkali metal silicates dissolve faster and should be used for best results when the alkali metal silicate is added in solid form. In instances where an anhydrous alkali metal silicate is used, it may be desirable to dissolve it in water and then add the solution to the aqueous medium. Sodium metasilicate is preferred and usually a hydrated sodium metasilicate such as the pentahydrate gives the best results.

Carbonate ion and/or bicarbonate ion should not be present in the aqueous medium in substantial concentrations as the calcium ion and magnesium ion are precipitated in the form of their respective carbonates. The free carbonate ion and/or bicarbonate ion concentrations in the aqueous medium should not exceed about 10 parts per million by weight based upon the combined weight of the water and the ingredients added thereto and for this reason, the alkali metal silicates should be substantially free of carbonate ion and bicarbonate ion. A small amount of precipitated calcium carbonate and/or magnesium carbonate may be present in the aqueous medium provided additional calcium ion and magnesium ion are available to meet the above defined concentrations.

Distilled water and/or deionized water are usually preferred over a natural or untreated water when preparing the aqueous medium. In instances where water is used which contains substantial initial concentrations of alkaline earth metal ions, then this should be taken into consideration in calculating the amounts of the sources of calcium ion and magnesium ion which are necessary to arrive at the final concentrations previously discussed.

An electrolyte which aids in the preparation of colloidal suspensions may be present in the aqueous medium at the time of admixing the alkali metal silicate therewith. Examples of electrolytes include those used in preparing prior art colloidal suspensions such as the alkali metal halides, sulfates and bisulfates. Sodium chloride, sodium sulfate and sodium bisulfate are usually preferred. The electrolyte should be added in small amounts such as, for example, about 0.00001-0.1 mole per liter, but often larger or smaller amounts may be present.

The conditions under which the alkali metal silicate is admixed with the aqueous medium and reacted with the sources of calcium ion and magnesium ion are not critical provided the reaction mixture is maintained in the liquid phase. The reaction temperature may be, for example, between the freezing point and boiling point of water under the existing pressure conditions. At atmospheric pressure, the temperature is usually about 10°-90° C and often a more convenient temperature is about 20°-50° C. In many instances, ambient or normal room temperature is satisfactory.

The degree of agitation is not critical, and mild to vigorous agitation may be employed during addition of the alkali metal silicate. For the best results, the aqueous medium should be agitated sufficiently to assure rapid and uniform admixing of the alkali metal silicate. After completing the addition of the alkali metal silicate, when desired the agitation may be continued for a sufficient period of time to assure complete reaction and aging of the resulting colloidal suspension, such as for approximately 1-5 minutes to one hour or longer.

Upon admixing the alkali metal silicate with the aqueous medium, it takes on a turbid appearance but in most instances no significant amount of visible precipitate is formed. The colloidal suspension of the reaction product thus produced should be strongly basic and may have a pH value of, for example, approximately 10-14 and preferably about 11-13, and for best results about 12. In view of this, the initial pH value of the aqueous medium containing the dissolved sources of calcium ion and magnesium ion is of importance and should be about 6-9 and preferably about 7-8. When necessary, it is possible to adjust the pH value of the aqueous medium to the foregoing levels either before during or after addition of the alkali metal silicate by adding bases such as sodium or potassium hydroxide, or mineral acids such as sulfuric or hydrochloric acid.

The colloidal suspension may be stored for several weeks or longer while awaiting the further treatment described hereinafter. In instances where the colloidal suspension is to be stored over a substantial period of time, the pH value should be maintained at the above described level and the storage vessel is preferably a tightly capped polyethylene bottle or other inert plastic container which prevents the contents from absorbing carbon dioxide from the atmosphere.

The colloidal suspension of the reaction product is not suitable for use as a catalyst as prepared and it should be agitated sufficiently in the presence of a micelle-forming surfactant to form catalyst-containing micelles. The degree of agitation, the length of the agitation period, and the amount of the micelleforming surfactant that is present in the colloidal suspension are controlled at levels favorable to the formation of micelles. For example, the surfactant may be present in an amount of about 0.001-0.1 mole per liter and preferably about 0.03-0.07 mole per liter for most surfactants. Smaller or larger amounts may be effective with some surfactants such as 0.0001 mole per liter or less, or 2.0 mole per liter or more. About 0.05 mole per liter often gives the best results with many surfactants.

The minimum period of agitation and the minimum degree of agitation that are required for micelle formation varies somewhat with temperature and the type and amount of surfactant. As is well understood in this art, gradually increasing these variants in the presence of an effective amount of the micelle-forming surfactant will result in micelle formation when the proper levels are reached. As a general rule, longer periods of agitation and/or more vigorous agitation are required to form micelles at lower temperatures approaching the freezing point of the colloidal suspension than at higher temperatures approaching the boiling point. In instances where the aqueous suspension has a temperature of approximately 50°-90° C., then mild agitation over a period of about 10-60 minutes is satisfactory. Often longer or shorter periods of mild to vigorous agitation may be employed such as from about 1-5 minutes to several hours at temperatures varying, respectively, between the boiling point and the freezing point. When desired, the agitation may be continued long after the catalyst-containing micelles are formed as continued agitation does not seem to have an adverse affect.

As a general rule, the micelle-forming surfactants known in the prior art may be used in practicing the present invention. Micelle-forming surfactants used in the emulsion polymerization of monomeric organic compounds are disclosed in the text *Synthetic Rubber*, by G. S. Whitby, et al, John Wiley & Sons Incorporated, New York (1954), and surface active agents in general are disclosed on pages 418-424 of the text *Organic Chemistry*, Fieser and Fieser, 2nd Edition, Reinhold Publishing Corporation, New York, New York (1950), the disclosures of which are incorporated herein by reference. Examples of surfactants disclosed in the above texts include the alkali metal soaps of long chain fatty acids, and especially the sodium and potassium soaps of fatty acids containing about 14-25 carbon atoms and preferably about 16-18 carbon atoms, and the sodium and potassium soaps of the rosin acids, abietic acid and the derivatives thereof. Other micelle-forming surfactants include fats and oils such as corn oil, cotton seed oil, castor oil, soy bean oil and safflower oil which have been fully or partially saponified with alkali metal bases to produce mixtures including saponified long chain fatty acids, the mono- or di-glycerides thereof, and glycerin.

Examples of synthetic micelle-forming surfactants include the sulfonates of long chain alcohols prepared by hydrogenation of naturally occurring fats and oils of the above types and especially sulfonated long chain alcohols containing about 10-20 and preferably about 12-14 carbon atoms, the alkali metal salts of the monosulfonates of monoglycerides such as sodium glyceryl monolaurate sulfonate, the sulfonates of succinic acid esters such as dioctyl sodium sulfosuccinate and the alkylaryl alkali metal sulfonates. Specific examples of presently preferred micelle-forming surfactants include sodium and potassium sulforicinoleate, tetrahydronaphthalene sulfonate, octahydroanthracene sulfonic acid, butyl naphthalene sulfonic acid, sodium xylene sulfonate, alkyl benzene sulfonic acid and potassium benzene sulfonate.

Sulfated long chain hydroxycarboxylic acids containing about 14-25 carbon atoms and preferably about 16-18 carbon atoms, and sulfated fats and oils containing hydroxycarboxylic acids of this type produce exceptionally good micelle-forming surfactants. At least 25% of the hydroxyl groups and preferably at least 50% should be sulfated, and up to 95-100% may be sulfated. It is usually preferred that the sulfated oils and/or long chain hydroxycarboxylic acids be neutralized with an alkali metal base, and that the corresponding alkali metal salts be added to the colloidal suspension in the form of an aqueous solution. The aqueous solution may contain at least 25% of water and preferably at least 35-40% by weight. Much larger percentages of water may be present when desired such as 75-80% or more by weight.

A very active catalyst is produced when using sulfated castor oil as the micelle-forming surfactant (Turkey Red oil). Sulfated castor oil which has been purified sufficiently to be of U.S.P. or medicinal grade produces an exceptionally active catalyst. For the best results, the castor oil is reacted with about an equal weight of concentrated sulfuric acid (e.g., 20% by weight $H_2SO_4$) at a temperature of approximately 25°-30° C. The mixture may be reacted for about two hours with stirring and is then neutralized with sodium hydroxide solution. The reaction mixture separates into three layers, i.e., an upper layer which is a water solution, an intermediate or oily layer, and a white curdy precipitate. The intermediate oily layer is separated from the upper and lower layers, and may be added to the colloidal suspension as the micelle-forming surfactant in an amount, for example, of 0.001-0.1 mole per liter, and preferably about 0.005 mole per liter.

The activity of the catalyst may be increased very markedly by cooling the aqueous catalyst suspension to a temperature approaching the freezing point such as about 0–10° C., and then warming over one or more cycles. For best results, the aqueous catalyst suspension should be frozen and thawed over one or more cycles. The reason for the increased catalytic activity is not fully understood at the present time but cooling and then warming the aqueous catalyst suspension seems to increase the concentration of the catalyst-containing micelles and/or increases the catalytic activity thereof.

The aqueous suspension of the catalyst contains a relatively small percentage by weight of the active catalyst as produced. When desired, it may be concentrated by evaporating a portion of the water to produce a concentrated liquid catalyst suspension which may be stored and used more conveniently. It is also possible to prepare a dry catalyst concentrate by evaporating substantially all of the water. The preferred method of producing the dry catalyst concentrate is by flash evaporation using a technique analogous to that employed in preparing powdered milk. The catalyst concentrates produced upon partial or complete evaporation of the water content of the initially prepared aqueous suspension may be reconstituted by addition of water with little or no loss of catalytic activity. Preferably, the water is added to the dry catalyst concentrate under sufficiently vigorous conditions of agitation to assure that the catalyst micelles are resuspended and uniformly distributed.

In a further variant of the process for preparing the catalyst, at least one dissolved substance providing at least one amphoteric metal-containing ion is present in the aqueous medium at the time of reacting the alkali metal silicate with the substances providing calcium ion and magnesium ion. The substance or substances providing the amphoteric metal-containing ion or ions may be present, for example, in an amount sufficient to provide about 0.0001–10% and preferably about 0.01–0.5% by weight when calculated as the amphoteric metal oxide and based upon the weight of the alkali metal silicate. Preferred amphoteric metals include aluminum and/or zinc, and the preferred sources thereof include alkali metal aluminate and zincate of which sodium and/or potassium aluminate and/or zincate usually give the best results. The alkali metal aluminate and/or zincate may be added directly to the aqueous medium, or as the mineral acid salts, oxides and/or hydroxides which then form the alkali metal aluminate and/or zincate under the highly alkaline conditions that exist.

The aqueous catalyst suspension may be used in the concentration as produced, or it may be diluted with approximately 2–100,000 or more parts by weight of water prior to use. It is only necessary that the aqueous medium contain a catalytic amount of the catalyst and much larger than catalytic amounts may be present. For better results, in some instances the catalyst suspension as produced may be diluted with about 200–10,000 parts by weight of water, and for still better results in other instances, with about 500–1,000 parts by weight of water. The aqueous medium may, for example, have 0.000001–1% by weight and often about 0.0001–0.3% by weight of the catalyst, but larger or smaller amounts may be present. In some instances, the aqueous medium contains about 0.001–0.1% or 0.004–0.08% by weight of the catalyst, and in other instances about 0.006–007% by weight. The weight or weight percent of the catalyst is calculated on a dry solids basis, i.e., the total weight of the catalyst ingredients in the aqueous catalyst suspension as produced after removal of the water. The dry catalyst solids or liquid catalyst concentrate may be admixed with water and/or a micelle forming surface active agent to provide a catalytically effective catalyst micelle concentration such as in the quantities previously discussed. The pH of the diluted aqueous catalyst suspension to be used may be adjusted to a desired value by addition of a mineral acid such as sulfuric acid or a strong base such as alkali metal hydroxide. This variant is of importance when the catalyst suspension should be approximately neutral as used for a given purpose. This variant is also of importance where the aqueous catalyst suspension, when used for a specific purpose, should be strongly acidic or basic for better results.

THE PREPARATION OF SOLUTIONS OF CATALYST TREATED LIGNITE

The aqueous solutions of catalyst treated lignite for use in practicing the method of the invention may be prepared as described hereinafter.

The lignite is intimately contacted in particulate form with an aqueous medium containing a catalytically effective amount of the novel catalyst described above. The lignite has active sites which are capable of reacting with at least one component of the aqueous medium in the presence of the catalyst, and it is contacted with the aqueous medium under liquid phase conditions until substantially all or a desired proportion of the active sites react. Thereafter, the lignite may be further treated as more fully described below.

The lignite need not be pretreated prior to treating with the aqueous medium other than, when desired, crushing or otherwise reducing it to a suitable particle size. The particle size is not critical and may vary over wide ranges as the aqueous medium has remarkable penetration properties and is capable of penetrating large lumps. The particle size may be, for example, from 1 inch to −300 mesh (Tyler Screen) and preferably is about −10 mesh to −200 mesh, and for many applications is from −50 mesh to −100 mesh. It is understood that particles as large as 2, 3 or 4 inches, and often mine run lignite, may be treated but longer periods of contact with the aqueous medium may be necessary to allow sufficient time for adequate penetration and reaction. Also, particle sizes smaller than −300 mesh may be treated but the expense of grinding the lignite to such a fine particle size usually outweighs any advantages that are gained. The volume ratio of aqueous medium to lignite may vary over wide ranges. It is usually preferred that the aqueous medium be present in sufficient volume to allow the particles to be easily agitated therein such as by means of a prior art stirring or agitating device. The concentration of the catalyst in the aqueous medium also may vary over wide ranges as it is only necessary that a catalytic amount be present. Suitable catalyst concentrations are discussed in the above section relating to the preparation of the catalyst. The pH value of the aqueous treating medium may vary from about 1 to 13.5. The initial pH value is preferably greater than 7, and is usually about 8–11. There is a tendency for the pH value to decrease as the reaction proceeds to about 5–6. If desired, the pH value of the aqueous medium may be adjusted as the reaction proceeds by addition of a base such as an alkali metal hydroxide to thereby partially or fully restore the initial pH value. Sodium, potassium or ammonium hydroxides are useful for this purpose and sodium hydroxide is usually preferred.

The temperature of treatment may likewise vary over wide ranges and may be, for example, between the freezing point and the boiling point of the aqueous medium under the existing pressure conditions. Usually atmospheric pressure is preferred, and in such instances, the aqueous medium may have a temperature of approximately 0° C. to 100° C. and is often about 20°-60° C. Surprisingly, lower temperatures of treatment such as 0°-10° C. appear to enhance the rate and degree of oxidation and thus lower temperatures may be preferred in instances where a maximum amount of oxidation is desired. Higher temperatures than 100° C. may be employed under superatmospheric pressure. Provided that the pressure is sufficient at the existing temperature to maintain liquid phase conditions, the temperature may be 100°-200° C. or higher but such extreme reaction conditions are not necessary and are usually avoided.

Inexpensive reaction vessels or open vats, with or without agitators and other simple auxiliary equipment, are satisfactory and may be used with good results. The period of treatment may be varied over wide ranges. It is only necessary that the aqueous medium be intimately contacted with the lignite for a period of time sufficient for the reaction to occur and continued treatment is not deleterious. The minimum period of treatment will vary to some extent with the remaining conditions, such as the particle size of the lignite, the concentration of the catalyst, the pH value of the aqueous medium and the reaction temperature. The period of treatment may vary, for example, from approximately 15 minutes or less to 24 hours or more but it is usually from about 1 to 3 hours. As a general rule, the amount of oxidation increases with time provided all of the remaining conditions of treatment remain the same. Lignite has active sites or carbon atoms such as carbon-to-carbon double or triple bonds, carbon-to-oxygen bonds, carbon-to-sulfur bonds, carbon-to-nitrogen bonds, carbon-to-metal bonds, carbon attached to an electronegative group, and carbon bonded or otherwise attached or attracted to a dissimilar substrate which is a component of the lignite. The catalyst of the present invention causes the liquid water in the aqueous treating medium to exhibit very unusual and heretofore unrecognized properties in the presence of lignite having the aforementioned active carbon atoms or active sites. While the exact nature of the reaction is not known at the present time, it appears that water or some component of water reacts with or alters the active carbon atoms or active sites to thereby produce pronounced chemical and/or physical changes. For example, the lignite may be oxidized to produce carboxylic acids and especially humic acids. It is also possible to fix nitrogen in the presence of an atmosphere containing elemental nitrogen. Additionally, combustable sulfur, nitrogen, and deleterious substances in general are altered to permit their removal by prior art techniques such as by extraction in the aqueous treating medium or with solvents subsequent to the treatment. Additionally, metal values present in the lignite are rendered soluble or solubilized. The treated particles have a much higher water content than before treatment. Following treatment, the aqueous treating medium contains the water soluble constituents of the treated lignite.

When the aqueous medium containing the catalyst is contacted with the lignite there is a period of activation during which there is little or no reaction. This activation period may be eliminated or reduced markedly by pre-treating a fresh catalyst suspension with a small portion of the lignite, or by using a recycled catalyst solution from a previous treatment. In a preferred variant, all or part of the aqueous catalyst suspension is recycled so that an activated catalyst is always available for contacting with fresh portions of the lignite. The activated aqueous catalyst suspension thus produced is much more effective.

In a further variant of the invention, the lignite is treated with an oxidizing agent before, during or following treatment with the aqueous medium containing the catalyst. The oxidizing agent may be air, elemental oxygen, ozone, peroxides such as hydrogen peroxide or the alkali metal peroxides, or other suitable oxidizing agents. The lignite is reacted with the oxidizing agent in an amount to partially oxidize or artificially weather it without combustion. For example, air or elemental oxygen may be bubbled through the aqueous medium while in contact with the lignite, or the lignite may be intimately contacted with air or elemental oxygen at elevated temperature prior to treatment with the aqueous medium. The oxidation of the lignite often may be enhanced by treating with the aqueous catalyst suspension at temperatures approaching the freezing point, such as about 0°-10° C. and preferably about 0°-4° C. The degree of oxidation is also often controlled to some extent by the materials used in constructing the reaction vessel and the materials of construction of auxiliary apparatus in contact therewith such as agitators. Surprisingly, constructing the equipment from nonconductors of electricity such as polyolefins results in a maximum degree of oxidation under a given set of operating conditions. Constructing the equipment from good conductors of electricity such as steel or other metals results in a minimum degree of oxidation for a given set of treating conditions, whereas constructing the equipment from glass or ceramic materials results in an intermediate degree of oxidation.

It is not necessary to separate the catalyst suspension from the treated lignite. For example, in many instances it is advantageous to evaporate the water content of the aqueous suspension, either at atmospheric pressure or preferably under reduced pressure, to thereby deposit the catalyst micelles on the treated lignite. When this is done, addition of water reactivates the catalyst micelles and the lignite may be subjected to a further treatment with the aqueous catalyst suspension until it is fully solubilized.

It is understood that the lignite is treated with an aqueous catalyst suspension until it is solubilized therein. The terms "solution", "solubilized," etc., as used herein when referring to this product are intended to embrace true solutions as well as aqueous media containing finely divided suspended substances which are not in true solution. It is also understood that the lignite solution, which contains the novel catalyst suspension described hereinbefore as an ingredient, may be substituted for the aqueous catalyst suspension per se in the method of the invention. It is only necessary to substitute a like amount of the catalyst-containing lignite solution for the aqueous catalyst suspension per se, based upon the dry solids weight of the catalyst present in each instance.

In practicing one presently preferred variant, the lignite is treated initially with the aqueous catalyst suspension following the aforementioned general procedure to produce a catalyst treated lignite product. This initial treatment may involve admixing the particulate lignite with the aqueous catalyst suspension and allowing it to soak at ambient temperature for a substantial period of time such as 1-24 hours and preferably for about 15 hours. While this initial soaking period is not essential, it appears to improve the uniformity of the results without producing adverse effects in instances where it is not needed. The initial pH value of the admixture is approximately 8-11, and during the soaking period, the pH value gradually drops to approximately 4-6.5 and preferably about 5-6. The admixture is then heated to an elevated temperature such as about 60°-100° C. and preferably about 90°-100° C. with stirring for approximately 0.5-5 hours and for best results approximately 1-3 hours. Thereafter a strong base such as sodium hydroxide is added in an amount to adjust the pH to the initial value of approximately 8-11 and preferably about 9-10, followed by continued heating with agitation until the pH value gradually drops again to approximately 4-6.5 and preferably about 5-6. In instances where the pH value remains above this latter range, then additional untreated lignite may be added in an amount to lower the pH level. The water is evaporated from the admixture without filtering as valuable ingredients are dissolved in the aqueous treating medium. Conventional air drying at ambient or elevated temperature or vacuum drying is usually preferred. The dry catalyst treated lignite product has the catalyst micelles initially present in the aqueous treating medium deposited thereon and it may be stored for long periods of time while awaiting further treatment and use. The aqueous catalyst suspension used in the aforementioned initial treatment of the lignite is preferably concentrated and may be a catalyst suspension as produced by Examples I-IV appearing hereinafter.

The dry catalyst treated lignite thus prepared may be admixed with additional aqueous catalyst suspension, which also is preferably concentrated and may be as produced by Examples I-IV, in an amount to prepare an oily paste-like admixture. Approximately equal parts by weight of the catalyst treated lignite and aqueous catalyst suspension usually produce good results. This paste-like admixutre may be easily dissolved in water and/or diluted catalyst suspension in amounts to produce a solution containing the desired amounts of dissolved lignite and/or catalyst on a dry solids basis for use in a given environment. It is only necessary that the catalyst be present in the catalytic amounts as described hereinbefore in the section on catalyst preparation, and the concentration of dissolved lignite may be as described below.

The concentrations of the catalyst suspension and the dissolved lignite solids in the solution may vary over extremely wide ranges. In a number of instances, the concentrations thereof are determined to some extent by the specific end use of the solution. Also, it is often advantageous to provide a concentrated solution which is diluted at the time of use. As a general rule, the concentration of catalyst solids in the solution is within the ranges aforementioned in the section of the preparation of the catalyst. The concentration of dissolved lignite in the solution may vary from about 0.01 to 0.1 part per million up to about 10% to 20% by weight. Solutions containing at least 500 parts per million, and preferably at least 600-700 parts per million, of dissolved lignite exhibit pronounced bacteriostatic and/or fungistatic properties and are often preferred for this reason. Solutions for general use usually contain about 0.5-500 parts per million, and preferably about 100-200 parts per million, of dissolved lignite and catalyst solids within the preferred ranges aforementioned, although more concentrated solutions may be provided initially for dilution. As a general rule, the solutions usually contain about 1-2% by weight or less of dissolved lignite.

Some naturally occurring lignites may contain metal values or other substances which are undesirable when the lignite solutions are used for certain purposes. In a further variant of the invention, such undesirable substances are removed from the lignite and/or rendered soluble in an extraction solvent in a pretreatment step with the catalyst suspension. For example, the lignite may be treated with an aqueous suspension of the catalyst following the usual practice until the undesirable substances are solubilized in the aqueous medium or rendered soluble in an extraction solvent. The period of treatment to accomplish this purpose may vary over wide ranges, such as from about 10 minutes to 10 hours or longer, or until the particles of lignite take on a weathered appearance similar to Leonardite and yet remain insoluble in the aqueous catalyst suspension and the extraction solvent. The treated lignite is separated from the catalyst suspension to thereby remove water soluble undesired substances. If water insoluble undesired substances are present, they may be removed by extraction with a suitable solvent. For example, aqueous mineral acids such as hydrochloric and sulfuric acid solutions may be used to remove acid soluble undesired constituents. Similarly, aqueous bases such as sodium, potassium and ammonium hydroxide may be used to remove undesired substances which are soluble in alkaline solutions. Additionally, liquid organic solvents such as liquid hydrocarbons, chlorinated hydrocarbons, alcohols, ketones and esters may be used to extract organic solvent soluble undesired substances. The resultant extracted lignite, which is now substantially free of undesired substances, is then further treated with the aqueous catalyst suspension until it is solubilized and a solution thereof may be prepared as previously discussed.

The concentrations of the catalyst and the solubilized lignite in the lignite solution are calculated by weight and on a dry solids basis. The lignite solids should be thoroughly air dried before weighing.

The invention is further illustrated by the following specific examples, which are for purposes of illustration only and are not limiting to the spirit or scope of the appended claims.

EXAMPLE I

This example illustrates one presently preferred process for preparing the novel catalyst used in practicing the invention.

Anhydrous calcium chloride in an amount of 0.66 gram and magnesium sulfate heptahydrate in an amount of 1.32 grams were dissolved in two liters of deionized water with stirring and warming until solution was complete. Then 95 grams of sodium silicate pentahydrate having a molecular ratio of sodium oxide to silicon dioxide of 1:1 were added to the solution with stirring and continued warming to produce a white colloidal suspension of the reaction product.

After setting for 10 minutes, the colloidal suspension was heated to 80° C. and sulfated castor oil in an amount of 201 grams was added with stirring. The average molecular weight of the sulfated castor oil was 940 and it contained 50% of water. The turbidity lessened somewhat as the colloidal suspension was heated at 80°-90° C. for one hour with vigorous stirring to produce catalyst micelles. The aqueous suspension of catalyst micelles thus prepared had a viscosity similar to that of water and it was used as a catalyst as noted hereinafter.

A dry or solid catalyst concentrate was prepared in a further run by evaporating water from the initially prepared aqueous catalyst suspension. The resulting dry catalyst concentrate was resuspended in water and there was no substantial loss of catalytic activity. In still other runs, the catalytic activity of the aqueous suspension of catalyst as initially prepared, the diluted aqueous suspension of catalyst, and the reconstituted aqueous catalyst suspension was enhanced by freezing and thawing.

EXAMPLE II

This example illustrates the preparation of additional catalyst suspensions.

Five suspensions of the catalyst were prepared from the same ingredients as used in Example I and following the general procedure of Example I. The ratios of ingredients were varied as follows:

| Ingredient | Amount of Ingredient | | | | |
|---|---|---|---|---|---|
| | Run 1 | Run 2 | Run 3 | Run 4 | Run 5 |
| Deionized water | 2 l | 1.5 l | 1.5 l | 1.5 l | 0.25 l |
| $CaCl_2$ | 0.66 g | 0.5 g | 0.5 g | 1.0 g | 0.5 g |
| $MgSO_4 . 7H_2O$ | 1.32 g | 1.0 g | 1.0 g | 2.0 g | 1.0 g |
| $Na_2SiO_3 . 5H_4O$ | 165 g | 132 g | 71 g | 185 g | 71 g |
| Sulfated Castor oil (approximately 50% by weight $H_2O$) | 100 ml | 150 ml | 150 ml | 200 ml | 150 ml |

The catalyst suspensions prepared by the above five runs were used as noted hereinafter.

EXAMPLE III

This Example illustrates a further presently preferred process for preparing the catalyst of the invention.

Anhydrous calcium chloride in an amount of 0.66 gram and magnesium sulfate heptahydrate in an amount of 1.32 grams were dissolved in one liter of soft water heated to 80° C. Then 95 grams of sodium silicate pentahydrate was added to the resulting solution with stirring to produce a suspension of finely divided particles of the reaction product. The sodium silicate pentahydrate contained approximately 0.12 gram of aluminum when calculated as $Al_2O_3$ and a somewhat smaller amount of zinc when calculated as ZnO.

The suspension of the reaction product was maintained at 80° C. and stirred for one-half hour. Then an aqueous solution prepared by admixing 75 grams of sulfated castor oil with 100 milliliters of water was added slowly with stirring. The stirring was continued for one-half hour thereafter while maintaining the reaction mixture at 80° C. to produce catalyst-containing micelles.

The sulfated castor oil contained 6.5–7% of organically combined $SO_3$ on a dry basis, 0.9–1.1% of combined alkali when calculated as sodium oxide, no free alkali, and 50%±1% of material volatile at 105° C., which was mostly water. The average molecular weight of the sulfated castor oil molecule was approximately 400 grams per mole.

The above prepared suspension of catalyst was placed in plastic containers awaiting testing and use. The catalyst suspension was tested and was rated as a superior catalyst. It was possible to add from 1,000 to 10,000 parts of water to a portion of the catalyst suspension and sill obtain excellent catalytic activity. A further portion of the catalyst suspension was frozen and thawed, and then tested. The cooling and warming steps enhanced the catalytic activity.

EXAMPLE IV

The general procedure of Example III was followed with the exception of using 0.33 gram of anhydrous calcium chloride rather than 0.66 gram, 0.66 gram of magnesium sulfate heptahydrate rather than 1.32 grams, and 45 grams of sodium silicate pentahydrate rather than 95 grams. The remaining ingredients and steps in the Example III procedure for preparing the catalyst were not changed.

The resulting catalyst suspension was approximately one-half as concentrated as that prepared in Example III. Upon testing, it was found to be as effective as the catalyst of Example III when calculated on a dry solid basis. Cooling the catalyst suspension to temperatures approaching the freezing point or freezing, following by warming or thawing, also had a beneficial effect upon the catalytic activity.

EXAMPLE V

This Example illustrates the preparation of solutions from lignite which are useful in practicing the method of the invention.

Lignite from the Havelock Mine, New England, N.D. was ground to minus 60 mesh (Tyler Screen) and 200 grams thereof was admixed with 250 ml of a catalyst suspension prepared in accordance with Example I and diluted with 1000 volumes of water. The admixture was treated for 2 hours at room temperature (72° F.) in a 1 quart Abbe Ball Mill using ¾ inch ceramic balls. Following the treatment, the reaction mixture was filtered to obtain a glassy black pitch-like solid residue of treated lignite particles and a yellow liquid treating solution having a pH of 6.7.

The treated lignite particles were extracted with acetone to produce a dark red solution and a residue of acetone extracted particles. The acetone extracted particles were further extracted with 3 M hydrochloric acid to obtain a yellow-orange acidic extract solution and an acid extracted residue.

The acid extracted char was further treated with 1 M sodium hydroxide solution and the mixture set to a jet-black pitchlike substance. The solution was filtered with difficulty to yield a black thick liquid and a sodium hydroxide treated residue. When the residue was washed with water, the solid material peptized and passed through the filter. Thus, substantially all of the lignite was solubilized.

EXAMPLE VI

This Example illustrates the preparation of an aqueous solution of catalyst treated lignite.

Weathered lignite having a particle size of minus 80 mesh (Tyler Screen) was admixed in an amount of 50 pounds with 2.50 ml of the catalyst suspension prepared in accordance with Example I and 8 gallons of hot soft water having a temperature of 150° F. The admixture was heated and stirred and after five minutes, the pH value was approximately 5. The admixture was allowed to set without heating for 12 hours and then 2 pounds of flake caustic (78% sodium hydroxide) was added. The admixture was stirred for approximately 5 minutes and the pH was 5–6. The wet catalyst treated lignite was air dried and stored in a plastic container.

The above prepared catalyst treated lignite was admixed in an amount of 298 grams with 307 grams of the catalyst suspension prepared in accordance with Example I. The resultant moist solid was stored in an airtight container while awaiting the preparation of a solution. Thereafter, 5 grams of this admixture was added to one gallon of soft water. Substantially all of the treated lignite dissolved forming a dark opague blue-black solution. The solution contained the catalyst in a concentration equivalent to diluting the catalyst suspension of Example I with 1000 volumes of water and it also contained 700 parts per million of the dissolved catalyst treated lignite. The pH value was 7.

EXAMPLE VII

This Example illustrates the treatment of lignite from Havelock Mine, New England, N.D. having a particle size such that 85% passed through a minus 85 mesh Tyler Screen.

An admixture of 70 pounds of the lignite, 300 ml of the catalyst suspension prepared in accordance with Example I and 8 gallons of soft water having a temperature of 150° F. was prepared. After 5 minutes of heating and stirring, the pH was 5 and 2.2 pounds of flake caustic soda (78% sodium hydroxide) was added. The pH of the resultant solution was 12 and after one-half hour of heating the pH was 11. The admixture was allowed to set for 12 hours.

Thereafter one-half of the treated lignite was air dried. A white encrustation appeared on the surface after drying. A second one-half portion of the treated lignite was kept moist with water for 2 days to determine if air oxidation continues provided the treated lignite is kept moist and basic. Upon testing, it was found that the air oxidation did continue. A white encrustation formed on the surface of the treated lignite when dry. The remaining one-third portion of the treated lignite was admixed with 2 gallons of hot soft water and thereafter 100 grams of sodium perborate was added. The temperature was 76° C. Thereafter, the treated lignite was air dried in the sun and no white encrustation developed on the surface. Lignite solutions are prepared from each of the above dry catalyst treated lignite products following the general procedure set out in the last paragraph of Example VI.

EXAMPLE VIII

This Example illustrates a further presently preferred process for preparing aqueous solutions of lignite which are useful in practicing the method of the invention.

Fifty pounds of North Dakota lignite was ground to minus 80 Tyler Mesh and admixed with five gallons of softened water containing 100 ml of the concentrated aqueous catalyst suspension as produced by Example I. The admixture was allowed to soak without heating for 15 hours. At the end of the soaking period, the pH value was 5 and the admixture was heated at 90°–100° C. with stirring for 3 hours. Sufficient flake sodium hydroxide was added to adjust the pH value to 11 and the heating and stirring was continued until the pH value had decreased to 5.

The water was removed from the resultant aqueous admixture of catalyst treated lignite by air drying. The dry catalyst treated lignite product thus prepared was stored in containers while awaiting the preparation of lignite solutions.

Approximately equal parts by weight of the catalyst treated air dried lignite and of the concentrated catalyst suspension prepared by Example I were admixed to produce a solid material having a paste-like consistency. Aqueous solutions of catalyst treated lignite were prepared from the paste having the following formulations:

TABLE I

| Ingredient | Formulation No. | | | |
| --- | --- | --- | --- | --- |
| | 1 | 2 | 3 | 4 |
| Catalyst Treated Lignite paste, grams | 7.32 | 2.9 | 300 | 300 |
| Concentrated Catalyst Suspension prepared by Example I, liters | None | 2.4 | 1.0 | 2.0 |
| Soft water, liters | 3.875 | 16.0 | 17.4 | 16.4 |

Certain of the above formulations were used in examples as noted hereinafter.

Additional solutions of catalyst treated lignite are prepared in further runs by following the general procedure of this Example with the exception of substituting the catalyst suspensions prepared in accordance with Examples II, III and IV for the catalyst suspension of Example I. All of the catalyst suspensions are active and are useful in solubilizing the lignite. Comparable results are obtained when the amount of the catalyst to be used is based upon dry catalyst solids.

EXAMPLE IX

This Example illustrates the use of the aqueous catalyst suspension prepared by Example I in transplanting plants by the method of the invention.

A diluted suspension of the catalyst is prepared by diluting the concentrated aqueous catalyst suspension as prepared by Example I with 1,000 volumes of water, and then adding one liquid ounce thereof to a gallon of water. The resultant diluted aqueous catalyst suspension is then intimately contacted with the roots of plants being transplanted as set out below.

A plot of soil suitable for use in growing garden vegetables and flowers is divided into a first portion and a second portion. The first and second portions are of substantially the same size and each portion is substantially equal in fertility initially. The first and second portions of the plot are plowed to loosen and pulverize the soil to a depth of approximately 4–6 inches and then rows are formed therein to receive the plants being transplanted.

Tomato, pepper, egg plant, marigold and zinnia seedlings of an age and size suitable for transplanting are divided into two groups. Openings are made in the rows of the first and second portions of the plot of a depth and spacing suitable for transplanting each species of plant. Thereafter, the roots of the plants in each of the first group are dipped into the diluted aqueous catalyst suspension, and then immediately planted in the first portion of the plot. Similarly, the roots of the plants in each of the second group of plants are dipped into plain water and then immediately transplanted in the second portion of the plot. The recommended spacing and transplanting procedures are followed in transplanting all plants and the conditions of transplanting are identical with the exception that the roots of the first portion of the plants are dipped in the diluted catalyst suspension of the invention prior to transplanting, and the roots of the second portion of the plants are merely dipped in plain water to provide comparative data.

Thereafter, the growing plants are cultivated under substantially identical conditions following the recommended practice for each species of plants. The growing plants are observed periodically during the growing season, and the yields are determined for the tomatoes, peppers and egg plants, and the number of flowers and the size and beauty thereof are determined for the marigolds and zinnias.

The plants in the first portion of the plot grow faster and are more vigorous and stronger, have a better color and general appearance, and are freer of disease than the plants grown in the second portion of the plot. The beneficial effects noted in the plants grown in the first portion of the plot continue throughout the normal lifespan of the plants. The yields of tomatoes, peppers and egg plants from the plants grown in the first portion of the plot are much higher than from those grown in the second portion of the plot. The marigolds and zinnias grown in the first portion of the plot have more flowers and the flowers are larger and more beautiful than from the marigolds and zinnias grown in the second portion of the plot. The plants grown in the first portion of the plot are also less affected by adverse weather, temperature, moisture level and other environmental conditions. Inasmuch as the first and second portions of the plot have received identical treatment with the exception that the roots of plants transplanted in the first portion are treated with the aqueous catalyst suspension, it is apparent that the presence of a catalytically effective amount of the catalyst increases the rate of survival of the transplanted plants, vigor and yield, and that it also provides the growing plants with an environment which results in greater resistance to disease and/or adverse environmental conditions.

EXAMPLE X

This Example illustrates the use of Formulation No. 3 of Example VIII in transplanting plants in accordance with the method of the invention.

The general procedure of this Example is the same as that of Example IX, with the exception of substituting diluted Formulation No. 3 prepared in accordance with Example VIII for the diluted catalyst suspension used in Example IX. Formulation No. 3 of Example VIII is diluted at the rate of one liquid ounce thereof per gallon of water, and the resultant diluted solution of catalyst and catalyst treated lignite is intimately contacted with the roots of plants to be transplanted as set out in Example IX.

The plants are observed periodically during the growing season and the yields are determined as in Example IX. The plants grown in the first portion of the plot are stronger and grow more vigorously, have a better color and general appearance, and are freer of disease than the plants grown in the second portion of the plot. These beneficial effects continue throughout the lifespan of the plants. The yields from plants grown in the first portion of the plot are much higher than the yields from the plants grown in the second portion of the plot. These beneficial effects on the plants grown in the first portion of the plot in this Example are even more marked than those observed and reported for the first portion of the plot in Example IX. Thus, the catalyst treated lignite in combination with catalyst per se produces even better results.

EXAMPLE XI

In a further series of runs, the general procedure of Example IX is repeated with the exception of using catalyst suspensions prepared by the procedures of Examples II – IV. Comparable results are obtained to those reported in Example IX on a dry catalyst solids basis.

In another series of runs, the test procedure of Example X is repeated with the exception of using catalyst suspensions on the same dry solids basis, but prepared by the procedures of Examples II – IV, for the preparation of lignite solutions in accordance with the procedures of Examples VI through VIII. The resulting lignite solutions are then substituted for Formulation No. 3 of Example VIII on a dry solids basis. Results comparable to those reported in Example X are obtained.

In a further series of runs, the test procedure of Example X is followed with the exception of substituting the lignite solutions identified as Formulations No. 1, 2 and 4 of Example VIII for Formulation No. 3 on a dry solids basis. Results comparable to those reported in Example X are obtained.

I claim:

1. A method of transplanting plants comprising intimately contacting the roots of plants being transplanted with water containing a catalytically effective amount of a catalyst, the said catalyst being prepared by a process comprising admixing a water soluble alkali metal silicate with an aqueous medium containing a dissolved substance which is a source of calcium ion and a dissolved substance which is a source of magnesium ion, the aqueous medium containing said dissolved substances in amounts to provide between about $1 \times 10^{-4}$ and $1 \times 10^{-1}$ mole per liter each of calcium ion and magnesium ion, the aqueous medium containing said dissolved substances in amounts to provide a molar ratio of calcium ion to magnesium ion between about 2.0:1.0 and 1.0:2.0, the alkali metal silicate having an alkali metal oxide to silicon dioxide ratio between about 0.9:1.0 and less than 2.0:1.0 and being admixed with the aqueous medium in an amount of about 0.05–2 moles per liter, reacting the alkali metal silicate with said dissolved substances providing calcium ion and magnesium ion to produce an aqueous suspension of finely divided particles of the reaction product, admixing a micelle-forming surfactant with the aqueous medium in an amount to form catalyst micelles comprising said finely divided particles upon agitating the aqueous medium, and agitating the aqueous medium containing the finely divided particles and surfactant to form said catalyst micelles.

2. The method of claim 1 wherein in the process for preparing the catalyst, said ratio of calcium ion to magnesium ion is between about 1.5:1.0 and 1.0:1.5.

3. The method of claim 1 wherein in the process for preparing the catalyst, said ratio of calcium ion to magnesium ion is about 1.0:1.0.

4. The method of claim 1 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion.

5. The method of claim 1 wherein in the process for preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion.

6. The method of claim 1 wherein in the process for preparing the catalyst, about 0.2–0.3 mole per liter of the alkali metal silicate is admixed with the aqueous medium.

7. The method of claim 1 wherein in the process for preparing the catalyst, the alkali metal silicate has an alkali metal oxide to silicon dioxide ratio between about 9.0:1.0 and 1.2:1.0.

8. The method of claim 1 wherein in the process for preparing the catalyst, the alkali metal silicate has an alkali metal oxide to silicon dioxide ratio of about 1.0:1.0.

9. The method of claim 1 wherein in the process for preparing the catalyst, about 0.001–0.1 mole per liter of the surfactant is admixed with the aqueous medium.

10. The method of claim 1 wherein in the process for preparing the catalyst, the surfactant comprises sulfated castor oil.

11. The method of claim 1 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion, the ratio of calcium ion to magnesium ion is between about 1.5:1.0 and 1.0:1.5, about 0.1–1 mole per liter of the alkali metal silicate is admixed with the aqueous medium, and the alkali metal silicate has an alkali metal oxide to silicon dioxide ratio between about 0.9:1.0 and 1.2:1.0.

12. The method of claim 1 wherein in the process for preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion, the aqueous medium contains about equimolar amounts of calcium ion and magnesium ion, about 0.2–0.3 mole per liter of the alkali metal silicate is admixed with the aqueous medium, and the alkali metal silicate has an alkali metal oxide to silicon dioxide ratio of about 1.0:1.0.

13. The method of claim 12 wherein in the process for preparing the catalyst, the alkali metal metasilicate is sodium metasilicate having an alkali metal oxide to silicon dioxide ratio of about 1.0:1.0.

14. The method of claim 12 wherein in the process for preparing the catalyst about 0.03–0.07 mole per liter of the surfactant is admixed with the aqueous medium.

15. The method of claim 14 wherein in the process for preparing the catalyst, the sufactant comprises sulfated castor oil.

16. The method of claim 15 wherein in the process for preparing the catalyst, the alkali metal metasilicate is sodium metasilicate having a sodium oxide to silicon dioxide ratio of about 1.0:1.0.

17. The method of claim 16 wherein in the process for preparing the catalyst, at least 25% of the hydroxy groups of the castor oil are sulfated, and about 0.03–0.07 mole per liter of the sulfated castor oil is admixed with the aqueous medium.

18. The method of claim 12 wherein in the process for preparing the catalyst, the alkali metal silicate is sodium metasilicate and it is admixed with an aqueous medium containing said dissolved substances in amounts to provide about $2.9 \times 10^{-3}$ mole per liter of calcium ion and about $2.7 \times 10^{-3}$ mole per liter of magnesium ion, about 0.25 mole per liter of sodium metasilicate having a sodium oxide to silicon dioxide ratio of about 1.0:1.0 is admixed with the aqueous medium, the aqueous medium contains not more than 10 parts per million by weight of carbonate ion and bicarbonate ion, the surfactant comprises sulfated castor oil and at least 50% of the hydroxy groups of the castor oil are sulfated, and about 0.05 mole per liter of the sulfated castor oil is admixed with the aqueous medium.

19. The method of claim 1 wherein the water intimately contacted with the roots of the said plants being transplanted also contains catalyst treated lignite, the lignite being pretreated with an aqueous medium containing the said catalyst defined in claim 1 until it is soluble in the said water.

20. The method of claim 19 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion, the ratio of calcium ion to magnesium ion is between about 1.5:1.0 and 1.0:1.5, about 0.1–1 mole per liter of the alkali metal silicate is admixed with the aqueous medium, and the alkali metal silicate has an alkali metal oxide to silicon dioxide ratio batween about 0.9:1.0 and 1.2:1.0.

21. The method of claim 19 wherein in the process for preparing the catalyst, the alkali metal silicate is sodium metasilicate and it is admixed with an aqueous medium containing said dissolved substances in amounts to provide between about $2.5 \times 10^{-3}$ and $3.0 \times 10^{-3}$ mole per liter each of calcium ion and magnesium ion, the aqueous medium contains about equimolar amounts of calcium ion and magnesium ion, about 0.2–0.3 mole per liter of the sodium metasilicate is admixed with the aqueous medium, and the sodium metasilicate has a sodium oxide to silicon dioxide ratio of about 1.0:1.0.

22. The method of claim 19 wherein in the process for preparing the catalyst, the alkali metal silicate is sodium metasilicate and it is admixed with an aqueous medium containing said dissolved substances in amounts to provide about $2.9 \times 10^{-3}$ mole per liter of calcium ion and about $2.7 \times 10^{-3}$ mole per liter of magnesium ion, about 0.25 mole per liter of sodium metasilicate having a sodium oxide to silicon dioxide ratio of about 1.0:1.0 is admixed with the aqueous medium, the aqueous medium contains not more than 10 parts per million by weight of carbonate ion and bicarbonate ion, the surfactant comprises sulfated castor oil and at least 50% of the hydroxy groups of the castor oil are sulfated, and about 0.05 mole per liter of the sulfated castor oil is admixed with the aqueous medium.

* * * * *